United States Patent

Kreifels et al.

[11] Patent Number: 5,488,949
[45] Date of Patent: Feb. 6, 1996

[54] DUAL SUCTION DEVICE

[76] Inventors: Kelly E. Kreifels, 16553 Dorcas St., Omaha, Nebr. 68130; Steven L. Carper, 5102 N. 105th St., Omaha, Nebr. 68134

[21] Appl. No.: 335,134

[22] Filed: Nov. 7, 1994

[51] Int. Cl.⁶ ................................................. A61M 16/00
[52] U.S. Cl. ............................ 128/207.14; 128/205.19; 128/207.16; 604/32; 604/248
[58] Field of Search ....................... 128/205.19, 207.14, 128/207.15, 207.17, 207.16, 911, 912; 604/32, 131, 248; 433/91, 95

[56] References Cited

U.S. PATENT DOCUMENTS

| | | | |
|---|---|---|---|
| 4,305,392 | 12/1981 | Chester | 604/98 |
| 4,795,447 | 1/1989 | Dodson | 604/268 |
| 5,033,464 | 7/1991 | Dicastilho | 128/205.19 |
| 5,143,062 | 9/1992 | Peckham | 128/207.14 |
| 5,181,505 | 1/1993 | Lew et al. | 128/200.26 |
| 5,253,643 | 10/1993 | Price | 128/207.14 |
| 5,257,620 | 11/1993 | Schermerhorn | 128/200.26 |
| 5,287,848 | 2/1994 | Cubb et al. | 128/200.26 |

*Primary Examiner*—Edgar S. Burr
*Assistant Examiner*—Eric P. Raciti
*Attorney, Agent, or Firm*—Zarley, McKee, Thomte, Voorhees & Sease; Mark D. Frederiksen

[57] ABSTRACT

A dual suction device includes an enclosed housing with a hollow interior cavity and an exhaust port formed in a rearward wall of the housing. A suction tube is pivotally mounted to the housing to pivot between a first position communicating with the exhaust port, and a second position sealed from the exhaust port. A tubular arm is also connected to the housing and fluidly connected to the interior cavity. A flap on the suction tube is moved in conjunction with pivotal motion of the suction tube to selectively alternate suction from the exhaust port between the tubular arm, when the suction tube is in the second position, and the suction tube, when the suction tube is in the first position.

5 Claims, 2 Drawing Sheets

DUAL SUCTION DEVICE

TECHNICAL FIELD

The present invention relates generally to apparatus for endotracheal suction and oral suction, and more particularly to an improved suction apparatus having two suction pods alternatively connected to a single suction source for selective suction through an endotracheal catheter and oral catheter.

BACKGROUND OF THE INVENTION

Various oral suction apparatus are well known in the prior art, and are utilized to clear a patient's mouth of secretions and foreign objects to clear a path for breathing. Because an oral suction apparatus is utilized in the oral cavity, it is not a critical requirement that the device be maintained in a sterilized condition for repeated uses on the same patient.

Endotracheal suction catheters are also well known in the prior art. Endotracheal suction apparatus include a sterilized catheter which is extended into a patient's lungs to suction secretions and/or blood present in the lungs. Because the endotracheal catheter is placed within the lungs, it must remain sterilized for each use.

One of the problems found in emergency situations at a hospital or at an ambulance location is that it is often necessary to repeatedly utilize both an oral suction device and an endotracheal suction device. However, once the health care worker has contacted the oral suction device, or other items, the hands are not sterile, and a new endotracheal apparatus would be required to maintain a sterilized condition. In addition, in emergency situations, the health care worker wastes valuable time in searching for either one or the other of the suction devices, when attempting to provide sterile apparatus for working on a patient.

SUMMARY OF THE INVENTION

It is therefore a general object of the present invention to provide a suction apparatus which includes two suction pods, one for endotracheal suction and the other for oral suction, on a single apparatus.

A further object is to provide a dual suction apparatus having a simple connection to a single source of suction.

Still another object of the present invention is to provide a dual suction apparatus with a mechanical connection to permit individual and alternate operation of each of the two suction pods.

A further object is to provide a dual suction apparatus which is economical to manufacture and refined in appearance.

These and other objects will be apparent to those skilled in the art.

The dual suction device of the present invention includes an enclosed housing with a hollow interior cavity and an exhaust port formed in a rearward wall of the housing. A suction tube is pivotally mounted to the housing to pivot between a first position communicating with the exhaust port, and a second position sealed from the exhaust port. A tubular arm is also connected to the housing and fluidly connected to the interior cavity. A flap on the suction tube is moved in conjunction with pivotal motion of the suction tube to selectively alternate suction from the exhaust port between the tubular arm, when the suction tube is in the second position, and the suction tube, when the suction tube is in the first position.

DESCRIPTION OF THE PREFERRED EMBODIMENT

Figure 1:
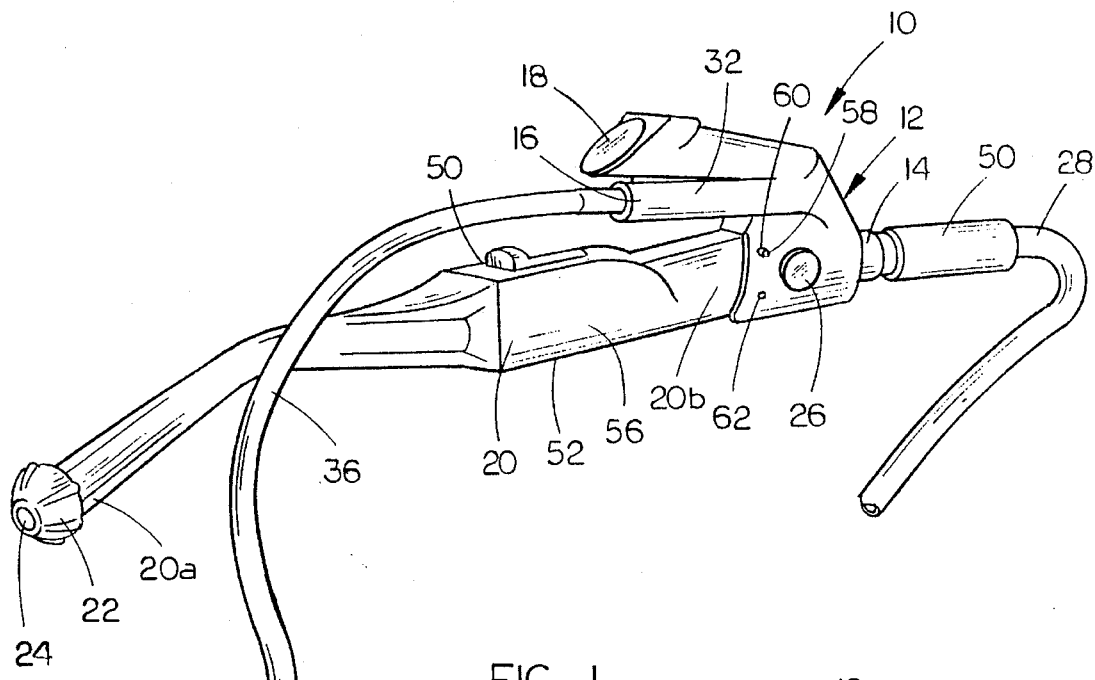
FIG. 1 is a perspective view of the invention with the oral suction port in an operable position.

Referring now to the drawings, and which similar or corresponding parts are identified with the same reference numeral, and more particularly to FIG. 1, the dual suction device of the present invention is designated generally at 10 and includes a housing 12 having a rearwardly projecting exhaust port 14, a forwardly projecting catheter port 16, a thumb valve 18 and an oral suction tube 20 pivotally connected to housing 12.

Figure 2:
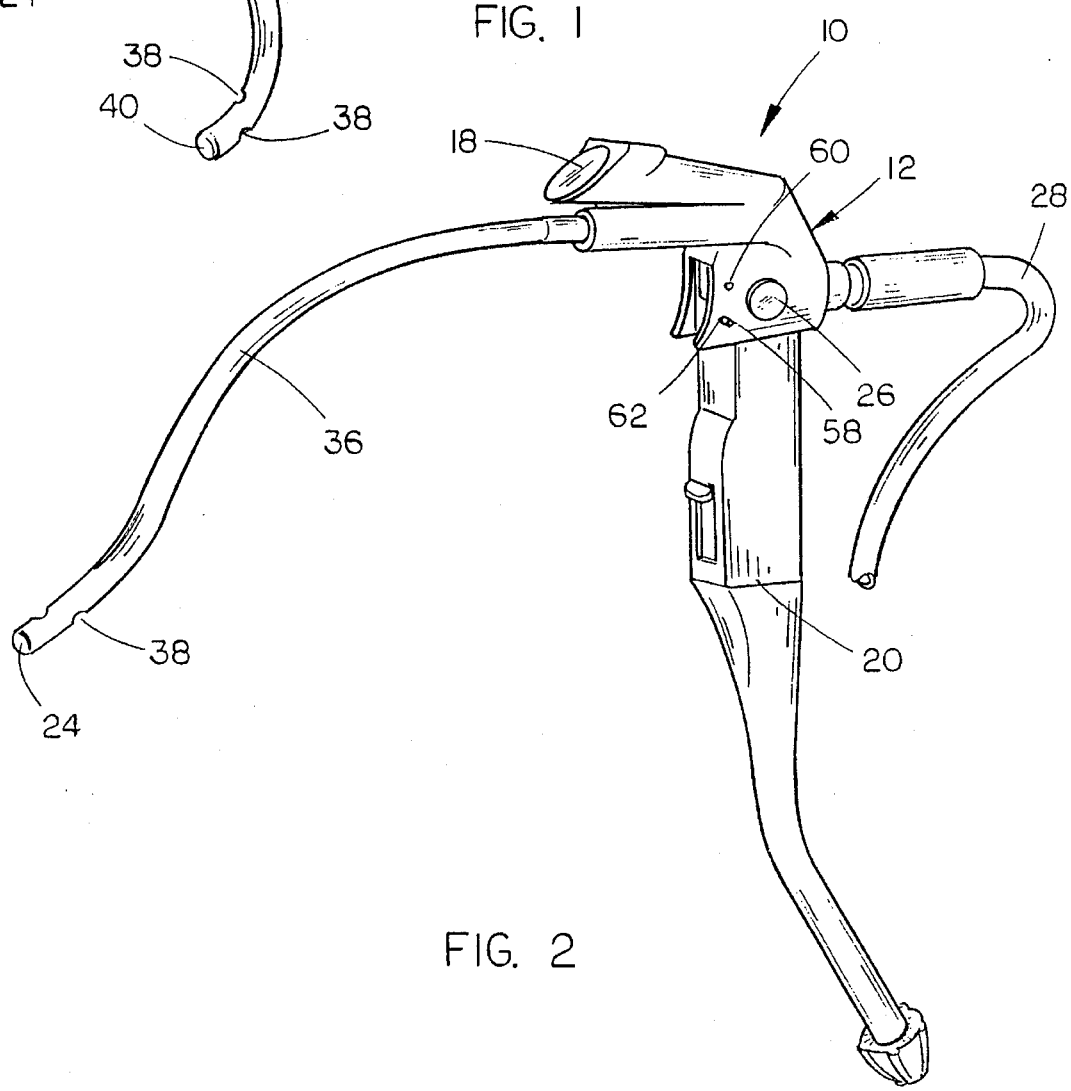
FIG. 2 is a perspective view of the invention with the endotracheal port of the apparatus in operable position.

Oral suction tube 20 is an elongated member having a head portion 22 at the forward end 20a thereof, with an intake opening 24 formed in the head portion 22 to receive fluid and materials from the oral cavity of the patient. The rearward end 20b of oral suction tube 20 is pivotally connected via pivot pin 26 within housing 12 for pivotal movement between an operable position aligned with exhaust port 14, as shown in FIG. 1 and a storage position generally perpendicular to the axis of port 14, as shown in FIG. 2.

A resilient flexible tube 28 is removably connected to exhaust port 14 with a connector 30, in a conventional fashion. Tube 28 extends to a source of suction (not shown) to provide dual suction device 10 with a suction.

Housing 12 includes a pair of forwardly and upwardly projecting tubular arms 32 and 34, respectively, extending from the juncture of suction tube 20 at housing 12. The forward end of first tubular arm 32 has catheter port 16 formed thereon which removably receives a conventional endotracheal catheter 36. The forward end of second tubular arm 34 has thumb valve opening 18 formed therein which permits placement of a thumb over opening 18 to close the opening and redirect air flow through first tubular arm 32 as discussed in more detail hereinbelow.

Endotracheal catheter 36 is of conventional manufacture, having lateral orifices 38 and an axial orifice 40 in the distal end 36b thereof. Proximal end 36a of endotracheal catheter 36 is removably attached to catheter port 16 on first tubular arm 32 in a conventional fashion.

Figure 3:
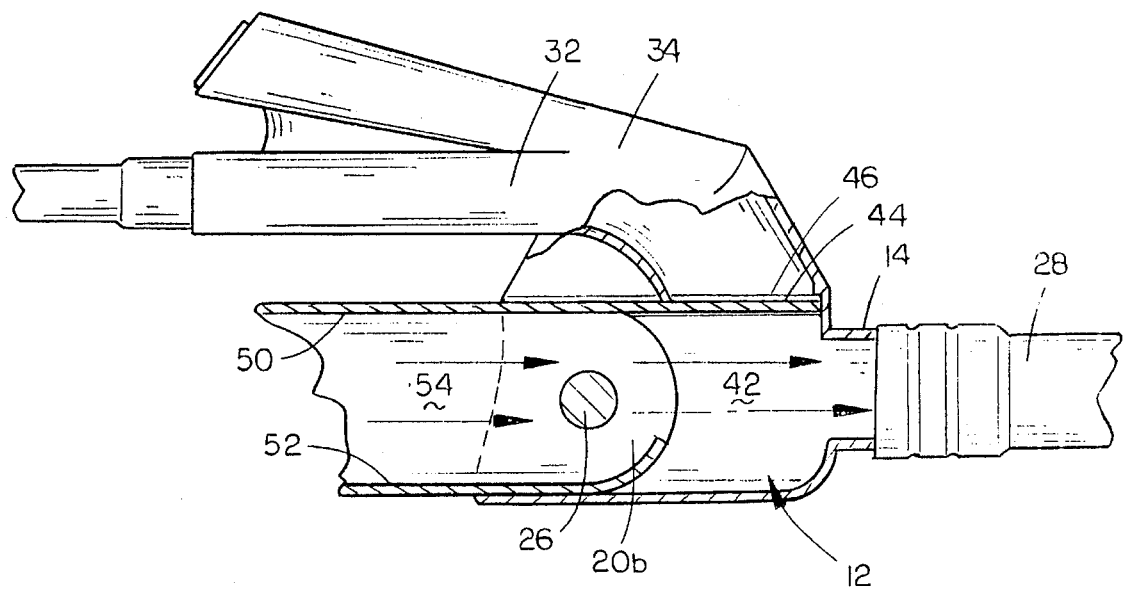
FIG. 3 is a vertical sectional view through the apparatus.
Figure 4:
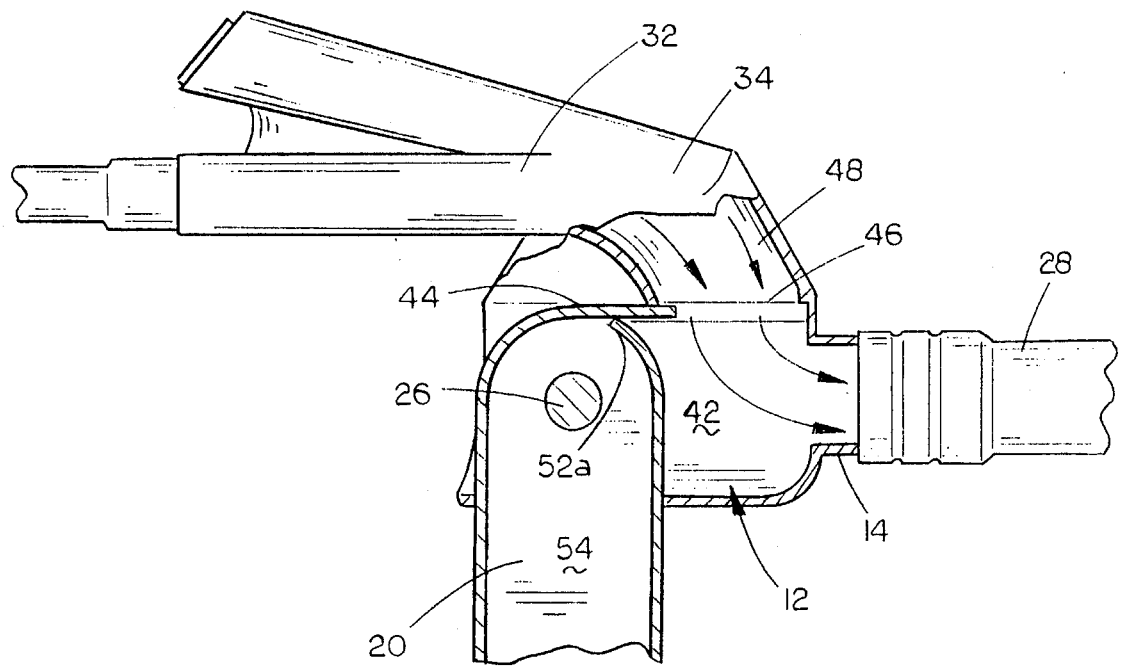
FIG. 4 is a vertical sectional view similar to FIG. 3, but with the apparatus moved to a second position.

Referring now to FIGS. 3 and 4, housing 12 includes a central cavity 42 fluidly connected through exhaust port 14 to exhaust tube 28. Rearward end 20b of oral suction tube 20 includes a flexible flap 44 journaled within a pair of opposing grooves 46 formed in opposing interior walls of housing 12 for slidable movement therealong. Flap 44 is slidable within grooves 46 between a first position, shown in FIG. 3, pneumatically sealing central cavity 42 from air passageway 48 leading to first and second tubular arms 32 and 34, and a second position, shown in FIG. 4, fluidly connecting passageway 48 with central cavity 42.

Flap 44 forms an extension of an upper wall 50 of tube 20, and opposes a lower wall 52. A pair of side walls 54 and 56 form tube 20. As shown in FIG. 3, the rearward end 20b of suction tube 20 is open to permit air flow from tube 20 through central cavity 42 and thence out exhaust port 14. When tube 20 is oriented in position 1, as shown in FIG. 3, flap 44 seals passageway 48 such that all suction is directed through oral suction tube 20. As suction tube 20 is pivoted on pivot pin 26, to the second position shown on FIG. 4, flap 44 will be retracted along grooves 46 while the rearward end of lower tube wall 52 is pivoted upwardly about pivot pin 26. When oral suction tube 20 is moved to position 2, the rearward end 52a of lower wall 52 will be in sealed contact with flap 44 to prevent air flow from air suction tube 20 to main cavity 42. Thus, all air flow is directed through air passageway 48 and thence to exhaust port 14. Referring once again to FIG. 1 and 2, a spring loaded pin 58 projects outwardly from side wall 56 and is journaled through one of two apertures 60 or 62 in the side wall of housing 12, to lock oral suction tube 20 in either the first position (shown in FIGS. 1 and 3) or the second position (shown in FIGS. 2 and 4). Depressing pin 58 permits pivotal movement of suction tube 20 in a well known manner.

In operation, dual suction device 10 is connected to a suction tube 28 extending from a suction canister or other suction source, via exhaust port 14. Oral suction tube 20 is oriented in the first position shown in FIG. 1 to provide suction through intake opening 24 in head portion 22. Suction tube 20 is utilized to clear any materials which may be present within a patient's mouth. Once the oral cavity is cleared, the physician is then able to place an endotracheal tube into the patient's lungs, as needed. To accomplish this task, pin 58 is depressed to permit oral suction tube 20 to be pivoted to the second position, shown in FIG. 2, and locked into position by the journaling of pin 58 in aperture 62. The endotracheal suction catheter 36 is then removed from a sterile package and attached to catheter port 16 on first tubular arm 32. The catheter is then positioned appropriately within the patient's lungs, and the physician may produce suction within catheter 36 by placing the thumb over thumb valve opening 18 on second tubular arm 32. As shown in FIG. 4, closing off thumb valve opening 18 will cause all suction to be directed through first tubular arm 32 and endotracheal catheter 36.

If it is again necessary to remove fluid or materials from the oral cavity, the physician's thumb is removed from opening 18, catheter 36 is disconnected from first tubular arm 32, with the distal end remaining in the patient's lungs. The oral suction tube 20 is then pivoted to the first position, by depressing pin 58 until it locks in aperture 60, thereby redirecting the suction flow of air from the oral suction tube 20. Thus, dual suction device 10 provides quickly interchangeable suction between an oral suction tube and an endotracheal catheter utilizing a single source of suction. In addition, the sterile catheter 36 is not contaminated during this interchanging of the suction duties of dual suction device 10.

Whereas the invention has been shown and described in connection with the preferred embodiment thereof, many modifications, substitutions and additions may be made which are within the intended broad scope of the appended claims.

We claim:

1. A dual suction device, comprising:

an enclosed housing having a hollow interior cavity and an exhaust port in a rearward wall thereof fluidly communicating with the cavity;

a suction tube connected to said housing and fluidly communicating with the interior cavity and having an orifice in a distal end thereof;

a tubular arm connected to said housing and fluidly communicating with said cavity and having an intake opening in a forward end thereof; and means within said housing for selectively and alternately sealing said suction tube and tubular arm, such that only one of said suction tube and tubular arm fluidly communicate with the housing cavity;

wherein said suction tube is pivotally mounted on said housing for pivotal movement between a first position and a second position, and wherein said means for selectively sealing said suction tube and tubular arm is connected to said suction tube and operable to seal said tubular arm when the suction tube is in the first position, and to seal the suction tube when the suction tube is in said second position.

2. The dual suction device of claim 1, wherein said means for selectively sealing said suction tube and tubular arm includes a flap connected to and extending rearwardly from a rearward end of said suction tube within said cavity, said flap slidable within said housing in response to pivotal movement of said suction tube, to seal the tubular arm from the housing cavity when the suction tube is pivoted to the first position, and to open an air passage from the tubular arm to the cavity when the suction tube is moved to the second position.

3. The dual suction device of claim 2, wherein said suction tube includes upper and lower opposing walls and opposing side walls forming said tube; wherein said flap extends rearwardly from a rearward end of the upper wall; and wherein said lower wall has a rearward end located to contact said flap and seal said suction tube when the suction tube is pivoted to the second position.

4. The dual suction device of claim 1, further comprising a second tubular arm connected to said housing and fluidly communicating with the first tubular arm, said second arm having an opening formed in a forward end thereof.

5. The dual suction device of claim 1, further comprising means for selectively locking said suction tube in the first and second positions.

* * * * *